US010482198B2

(12) United States Patent
Auerbach et al.

(10) Patent No.: US 10,482,198 B2
(45) Date of Patent: *Nov. 19, 2019

(54) GLOBAL MAPPING CATHETER CONTACT OPTIMIZATION

(71) Applicant: BIOSENSE WEBSTER (ISRAEL) LTD., Yokneam (IL)

(72) Inventors: Shmuel Auerbach, Kerem Maharal (IL); Aharon Turgeman, Zichron Ya'acov (IL)

(73) Assignee: Biosense Webster (Israel) Ltd., Yokneam (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/102,249

(22) Filed: Aug. 13, 2018

(65) Prior Publication Data

US 2018/0365355 A1    Dec. 20, 2018

Related U.S. Application Data

(63) Continuation of application No. 14/998,128, filed on Dec. 24, 2015, now Pat. No. 10,078,713.

(51) Int. Cl.
*A61B 34/10* (2016.01)
*G06F 17/50* (2006.01)
*A61B 5/0408* (2006.01)
*A61B 5/042* (2006.01)

(52) U.S. Cl.
CPC ........ *G06F 17/5009* (2013.01); *A61B 5/0408* (2013.01); *A61B 5/0422* (2013.01);
(Continued)

(58) Field of Classification Search
None
See application file for complete search history.

(56) References Cited

U.S. PATENT DOCUMENTS 5,546,951 A   8/1996 Ben-Haim
5,738,096 A   4/1998 Ben-Haim
(Continued)

FOREIGN PATENT DOCUMENTS

EP   1 421 913 A1   5/2004
EP   1 750 215 A1   2/2007
(Continued)

OTHER PUBLICATIONS

Ross, John, Jr., "Considerations Regarding the Technique for Transseptal Left Heart Catheterization", Circulation, vol. XXXIV, Sep. 1966, 34:391-399, Downloaded from http://circ.ahajournals.org/ by guest on Sep. 5, 2015.
(Continued)

*Primary Examiner* — Ankit D Tejani
(74) *Attorney, Agent, or Firm* — Vincent J. Serrao

(57) ABSTRACT

Cardiac catheterization is carried out by constructing a left atrial model of a heart of a living subject, selecting a global catheter that is dimensioned to conform to the left atrial model, representing the catheter in the left atrial model; extending the length axis of the catheter in the left atrial model to form an intersection with the foramen ovale, and reporting the intersection as a recommended site of transseptal puncture for insertion of the catheter therethrough.

1 Claim, 5 Drawing Sheets

(52) U.S. Cl.
  CPC ........ *A61B 34/10* (2016.02); *A61B 2034/107* (2016.02); *A61B 2034/108* (2016.02)

(56) References Cited

U.S. PATENT DOCUMENTS

| | | |
|---|---|---|
| 6,226,542 B1 | 5/2001 | Reisfeld |
| 6,301,496 B1 | 10/2001 | Reisfeld |
| 6,690,963 B2 | 2/2004 | Ben-Haim et al. |
| 6,814,733 B2 | 11/2004 | Yitzhack Schwartz |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,517,318 B2 | 4/2009 | Altmann et al. |
| 7,536,218 B2 | 5/2009 | Govari et al. |
| 7,756,576 B2 | 7/2010 | Levin |
| 9,576,107 B2 | 2/2017 | Bar-Tal et al. |
| 2007/0032826 A1* | 2/2007 | Schwartz ............... A61B 90/36 607/2 |
| 2007/0049817 A1 | 3/2007 | Preiss et al. |
| 2009/0177089 A1 | 7/2009 | Govari et al. |

FOREIGN PATENT DOCUMENTS

| | | |
|---|---|---|
| EP | 2 824 639 A2 | 1/2015 |
| WO | WO 96/05768 A1 | 2/1996 |

OTHER PUBLICATIONS

European Search Report dated Mar. 21, 2017 from corresponding European Patent Application No. 16206548.6.

\* cited by examiner

GLOBAL MAPPING CATHETER CONTACT OPTIMIZATION

CROSS REFERENCE TO RELATED APPLICATIONS

This application is a continuation of U.S. patent application Ser. No. 14/998,128, filed Dec. 24, 2015, now U.S. Patent Publication No. 2017/0185702, published Jun. 29, 2017, the entire contents of which is incorporated herein by reference.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to cardiac physiology. More particularly, this invention relates to the evaluation of electrical propagation in the heart.

2. Description of the Related Art

Cardiac arrhythmias such as atrial fibrillation are an important cause of morbidity and death. Commonly assigned U.S. Pat. Nos. 5,546,951, and 6,690,963, both issued to Ben Haim and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

When evaluating the left atrium, catheters, such as basket catheters may be introduced percutaneously via transseptal puncture. The document *Considerations Regarding the Technique for Transseptal Left Heart Catheterization*, J. Ross. Circulation October 1966; 34(3):391-9 points out a number of difficulties with this procedure, caused, for example, by lack of tactile appreciation of the movement of the catheter tip. As a result, the structures engaged by the catheter tip are not recognized, and the degree of pressure exerted against them is uncontrolled. For example, undesired contact of the needle with the posterior wall of the left atrium could occur. Moreover, the optimum site for puncture of the septum is influenced by such considerations as right or left atrial enlargement.

SUMMARY OF THE INVENTION

One method of mapping the left atrium is based on a global mapping catheter, typically in the form of a multi-electrode basket catheter, which is introduced into the left atrium by puncture of the interatrial septum, usually through the fossa ovalis. Basket catheters are relatively large in comparison to the left atrium and do not fit the human left atrium well. Consequently, mapping quality is impaired. These catheters have little to no deflection capabilities. The location of the puncture constitutes an anchoring point, which is a constraint, making it difficult or even impossible to manipulate a basket catheter into good contact with target regions of the atrium, particularly if the location of transseptal puncture is suboptimal.

Disclosed embodiments of the invention optimize the transeptal location of a global catheter in order to maximize the reach of a mapping catheter within the left atrium and the contact of the catheter with the left atrial wall.

There is provided according to embodiments of the invention a method, which is carried out by constructing a left atrial model of a heart of a living subject, selecting a global catheter that is dimensioned to conform to the left atrial model, representing the catheter in the left atrial model; extending the length axis of the catheter in the left atrial model to form an intersection with the foramen ovale, and reporting the intersection as a recommended site of transseptal puncture for insertion of the catheter therethrough.

According to an aspect of the method, constructing a left atrial model includes forming a 3-dimensional bounding box centered on a point of the left atrial model that corresponds to a center of mass of the left atrium, and selecting a global catheter includes referencing a database of global catheters to identify a selected catheter that conforms to the bounding box according to predefined box-conforming criteria.

According to another aspect of the method, representing the catheter in the left atrial model includes transforming the catheter into an ellipsoid and selecting a global catheter also includes determining that the ellipsoid approximates the bounding box according to the predefined box-conforming criteria.

According to still another aspect of the method, the predefined box-conforming criteria comprise a deviation of the major semi axis of the ellipsoid from the length dimension of the bounding box that is within a first range.

According to an additional aspect of the method, the predefined box-conforming criteria comp rise a deviation of a sum of the two minor semi-axes of the ellipsoid from a sum of the height dimension and the width dimension of the bounding box that is within a second range.

According to yet another aspect of the method extending the length axis of the catheter is performed by extending the major semi axis of the ellipsoid, and prior to extending the major semi axis of the ellipsoid performing a surface registration of the ellipsoid and the bounding box by adjusting the semi axes of the ellipsoid relative to the length dimension, the width dimension and the height dimension of the bounding box.

According to another aspect of the method, adjusting the semi axes of the ellipsoid includes minimizing a root-mean-square deviation between the surface of the ellipsoid and the borders of the bounding box.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Figure 1:
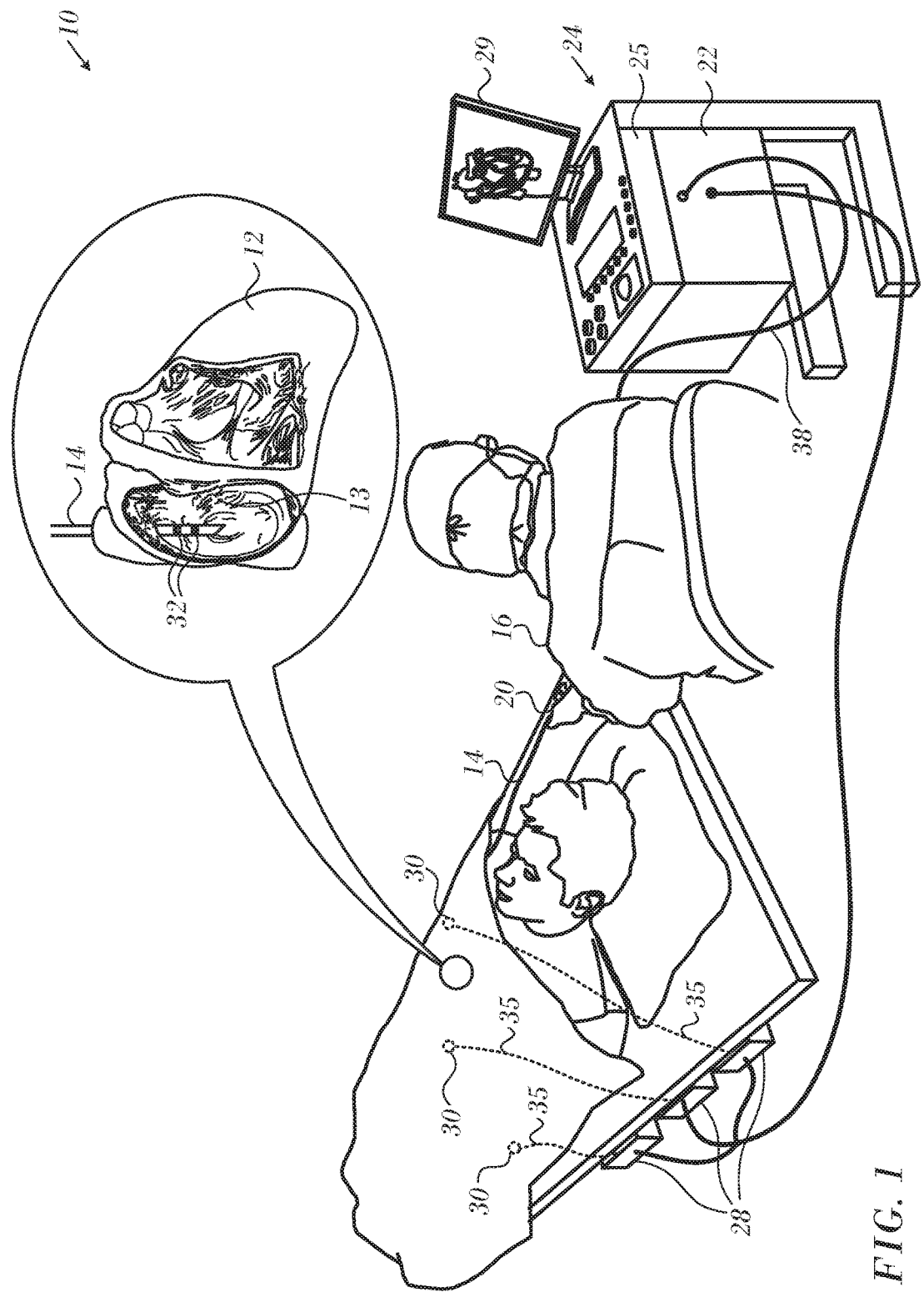
FIG. 1 is a pictorial illustration of a system for performing catheterization of a heart of a living subject in accordance with an embodiment of the invention.

Turning now to the drawings, reference is initially made to FIG. 1, which is a pictorial illustration of a system 10 for performing medical procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at a selected region of atrial septum 13 in preparation for septal puncture. When the catheter is in an operative position, electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference One commercial product embodying elements of the system 10 is available as the CARTO® 3 System, available from Biosense Webster, Inc., 33 Technology Drive, Irvine, Calif. 92618. This system may be modified by those skilled in the art to embody the principles of the invention described herein.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, which can be located in a console 24. The processor 22 may fulfill several processing functions as described below. Alternatively, the catheter 14 may be provided with collectors of electrical information, and circuitry in the console 24 may be accept and process the information. The EnSite™ system used with NavX surface electrode patches is an example. Indeed, the principles of the invention apply to many systems and methods that support navigation of a catheter into the left atrium via the interatrial septum.

Wire connections 35 link the console 24 with body surface electrodes 30 and other components of a positioning sub-system for measuring location and orientation coordinates of the catheter 14. The processor 22, or another processor (not shown) may be an element of the positioning subsystem. Electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter in magnetic sensors (not shown), using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images such as electroanatomic maps.

Figure 2:
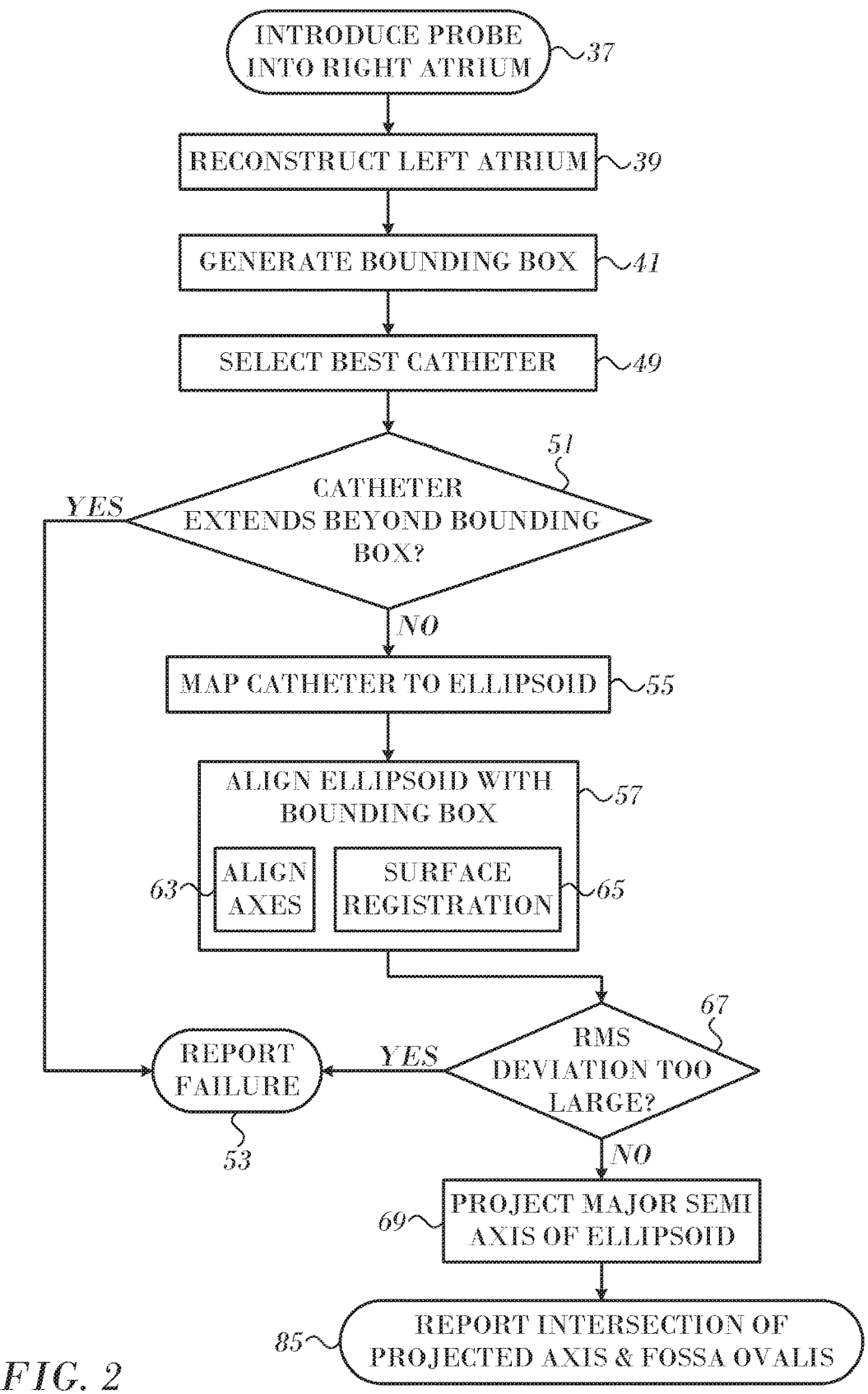
FIG. 2 is a flow chart of a method of optimizing contact between a cardiac probe or catheter with the interatrial septum, in accordance with an embodiment of the invention.

Reference is now made to FIG. 2, which is a flow chart of a method of optimizing contact between a cardiac probe or catheter with the interatrial septum in accordance with an embodiment of the invention. The process steps are shown in a particular linear sequence for clarity of presentation. However, some of them may be able to be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 37 a probe is introduced transcutaneously into the right atrium of the heart. Next, at step 39 a model of the left atrium is reconstructed, i.e., geometrically defined in 3-dimensional space. This can be accomplished by analysis of images from other modalities, i.e., segmentation from pre-acquired MRI or fluoroscopy images that have been registered with the atrial model. Registration of images acquired or prepared by different modalities is known, for example from U.S. Patent Application Publication No. 2007/0049817, and commonly assigned U.S. Pat. No. 7,517,318 to Altmann et al., which are herein incorporated by reference. Yet another method of generating the reconstruction is disclosed in commonly assigned U.S. Pat. No. 9,576,107, entitled Model Based Reconstruction of the Heart from Sparse Samples, which is herein incorporated by reference. In this method, the atrium shape is represented as the isosurface of a field function, defined at all points within a bounding domain Other methods of reconstruction are known in the art and may be used, for example the methods disclosed in U.S. Pat. No. 6,226,542 to Reisfeld, and U.S. Patent Application Publication No. 2009/0177089 by Govari et al., which are commonly assigned herewith and incorporated by reference. Alternatively the CARTOMERGE™ module and other facilities of the above-noted CARTO system can accomplish this step.

Figure 3:
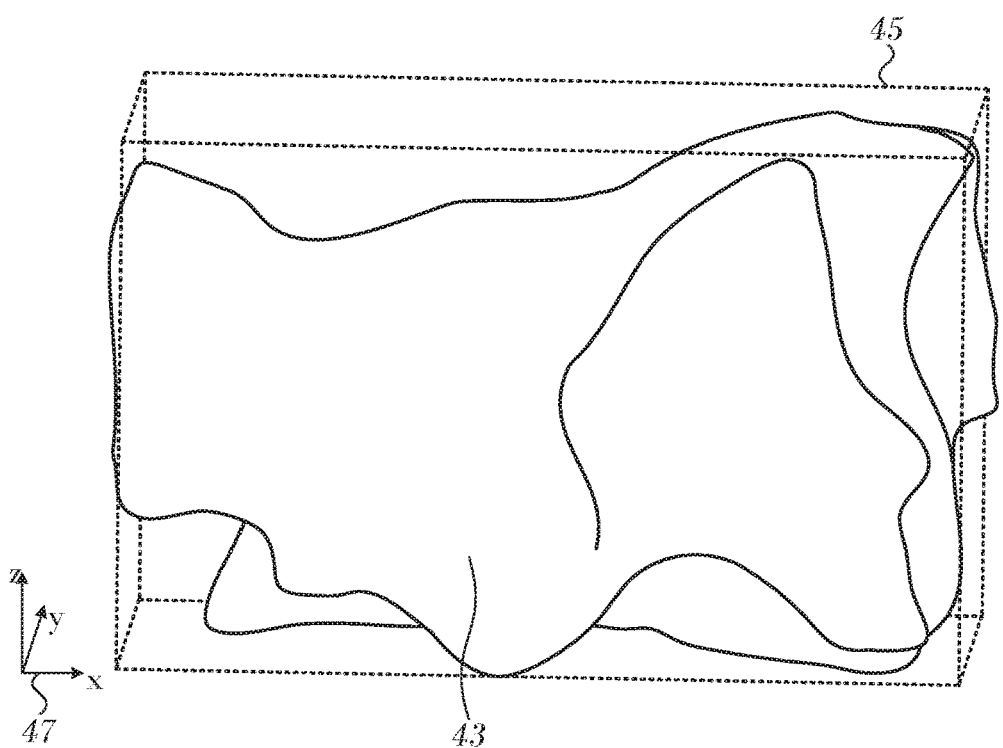
FIG. 3 is a reconstructed image of a left atrium in accordance with an embodiment of the invention.

Next, at step 41 a bounding box is established for the reconstructed left atrium by calculating the center of mass of the atrium, treating the atrium as an empty shell, excluding the pulmonary veins and defining three orthogonal axes that emanate from it. For example, the x-, y- and z-axes may align respectively with the length, width, and height of the bounding box, i.e., the x-axis aligns with the long axis of the bounding box. The center of the bounding box corresponds to a center of mass of the reconstructed left atrium. Reference is now made to FIG. 3, which is a reconstructed image of a left atrium 43, which was prepared in step 39, in accordance with an embodiment of the invention. A bounding box 45 has been established and encloses the left atrium 43. A reference coordinate system 47 is shown at the left of the bounding box 45.

Next, at step 49, A list of known global catheter models, including basket catheters is consulted. The catheter that best matches the bounding box of the left atrium that was produced in step 41 is selected from the list. Matching is done by comparing the lengths of the three axes of the catheter with those of the bounding box. Details of the matching procedure are presented below in the discussion of FIG. 6.

Next, at decision step 51, it is determined if a portion of the basket catheter selected in step 49, when placed within the bounding box, would extend beyond the box by more than a predefined distance threshold. Details of this step are described in the discussion of FIG. 6. If the determination is affirmative, then it is concluded that a satisfactory catheter could not be obtained from the list of available catheters. The procedure ends in failure at final step 53.

If the determination at decision step 51 is negative, then control proceeds to step 55. The basket catheter selected in step 49 is mapped to an ellipsoid.

Next, at step 57, the longest, intermediate, and shortest semi-axes are aligned with the x, y, z axis of the coordinate system 47 (FIG. 3) and with the bounding box 45 produced in step 41.

Figure 4:
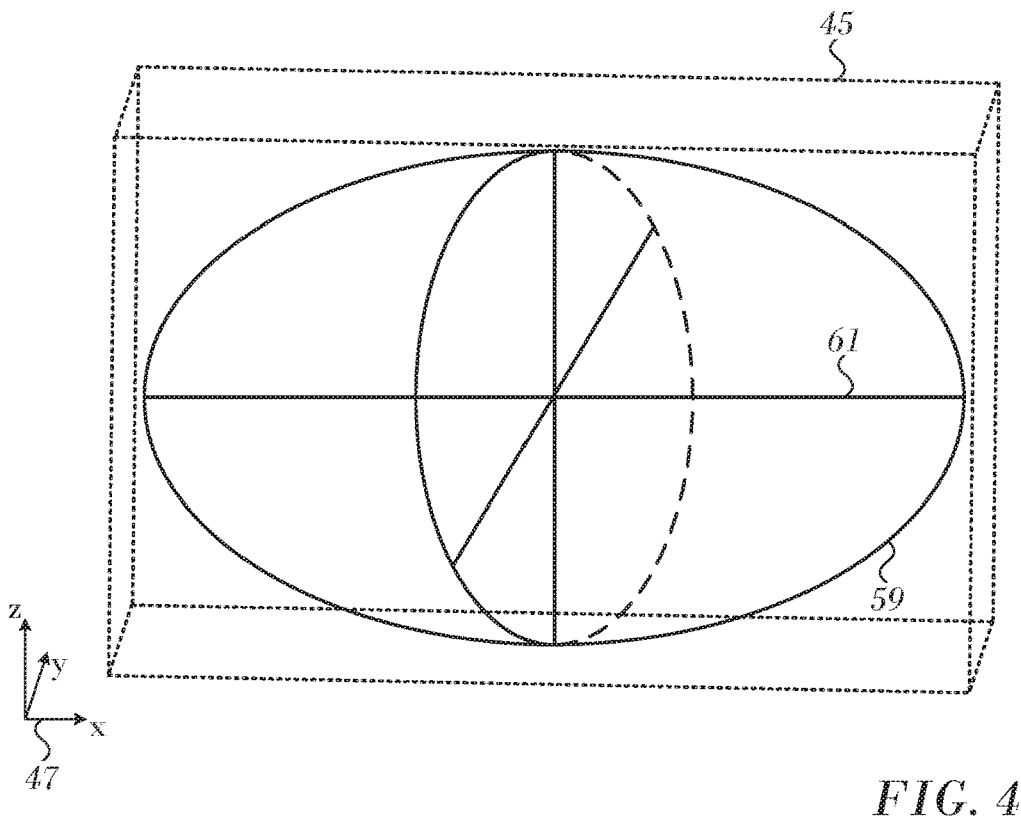
FIG. 4 is a diagram illustrating an ellipsoid as a transformation of a global catheter.

Reference is now made to FIG. 4, which is a diagram illustrating an ellipsoid 59 produced by transformation of catheter that was selected in step 49 in accordance with an embodiment of the invention. The ellipsoid 59, having major semi axis 61, is in registration with the dimensions of the bounding box 45 and aligned with its length, width and height axes.

Reverting to FIG. 2, step 57 is performed. Step 57 comprises steps 63 and step 65. At step 63 the image of the atrium generated in step 39 is placed in registration with the ellipsoid. This is done by superimposing the center of the ellipsoid with the center of mass of the left atrium and rotating the ellipsoid until the semi-axes of the ellipsoid align with the axes of the bounding box, i.e., the coordinate system 47.

In step 65 the axes of the ellipsoid are adjusted so as to minimize the root-mean-square deviation between the surface of the ellipsoid and the bounding box. The CARTOMERGE module of the above-noted CARTO 3 system can be used to perform step 65.

Next, at decision step 67, it is determined if the root-mean-square deviation determined in step 65 exceeds a predefined threshold. If the determination is affirmative, then control proceeds to final step 53, and failure is reported. The operator is advised that a transeptal location cannot be provided.

Figure 5:
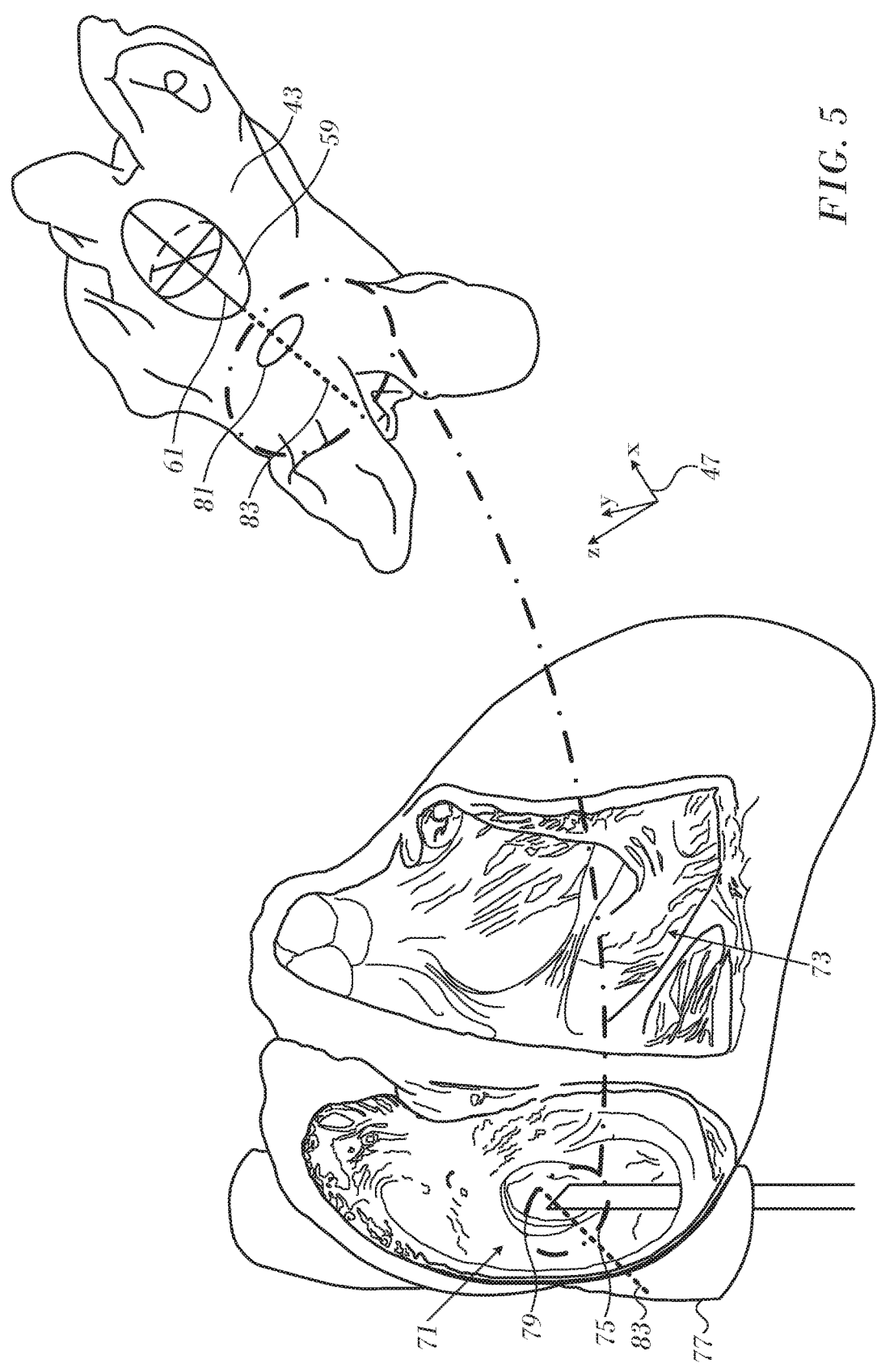
FIG. 5 is a composite diagram including a cut-away view of the heart and an atrial reconstruction in accordance with an embodiment of the invention.

If the determination at decision step 67 is negative, then the information developed in the preceding steps is used to calculate the best location for the transeptal puncture. Control proceeds to step 69. Step 69 can be appreciated by reference to FIG. 5, which is a composite, partially schematic diagram including a cut-away view of right atrium 71 and right ventricle 73 and an atrial reconstruction in accordance with an embodiment of the invention. The left portion of FIG. 5 illustrates the relevant anatomy semi-schematically. Probe 75 has been introduced through inferior vena cava 77 and its distal end approaches fossa ovalis 79. At the upper right of FIG. 5 is a diagram in which the ellipsoid 59 is superimposed on the reconstructed left atrium 43 produced in step 57 (FIG. 2). Major semi axis 61 is extended through fossa ovalis 81 as a broken line 83. The line 83 also appears on the cutaway view of the right atrium 71, where it is presented to the operator on monitor 29 (FIG. 1).

At final step 85, the intersection of the line 83 with the fossa ovalis 79 is reported as to the operator as a recommended puncture site.

Figure 6:
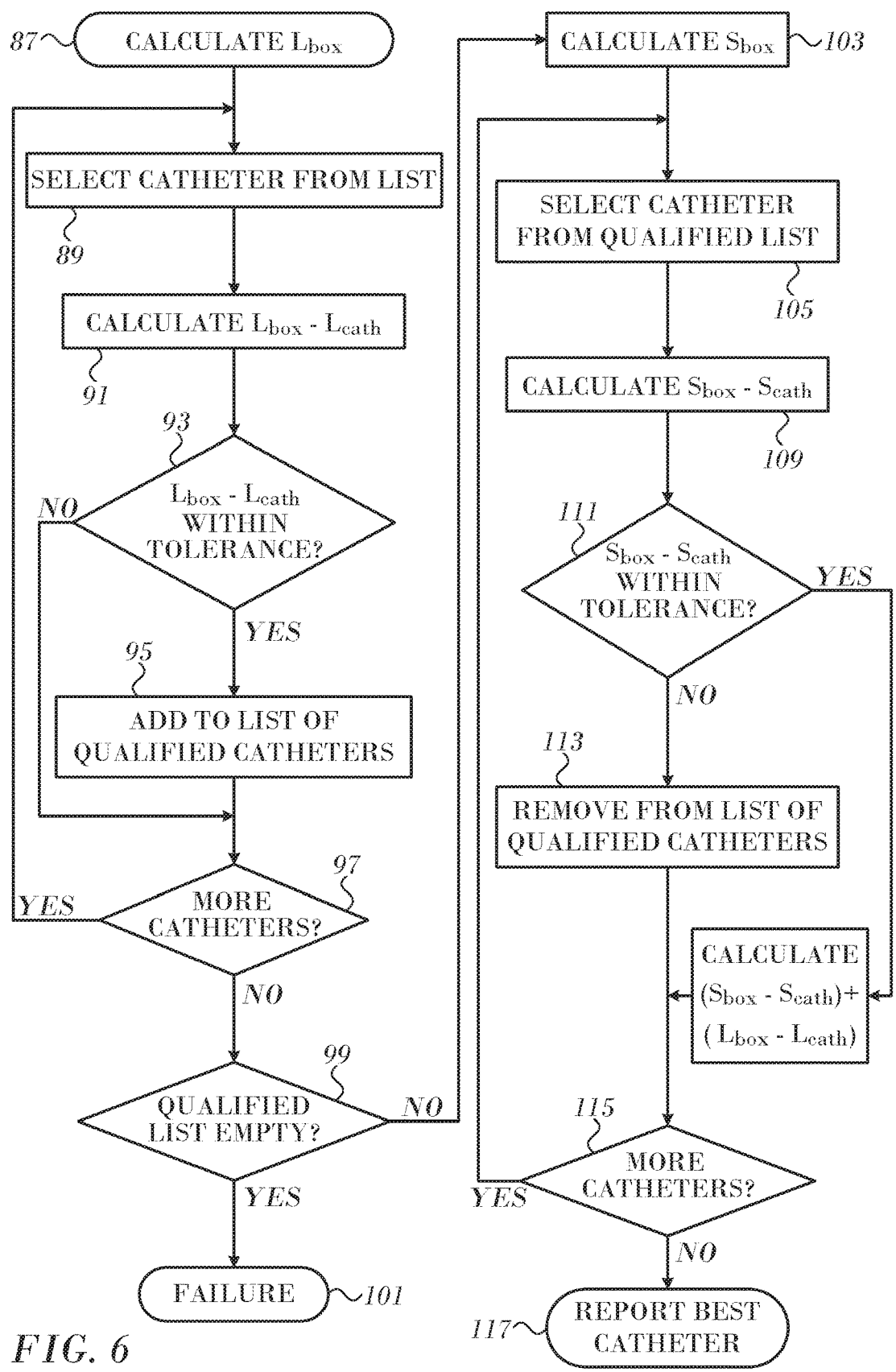
FIG. 6 is a flow chart of a method for identifying a catheter that best matches the left atrial anatomy of a subject in accordance with an embodiment of the invention.

Reference is now made to FIG. 6, which is a flow chart detailing step 49 (FIG. 2), in which a catheter that best suits the left atrial anatomy of a particular subject is selected from a list of catheters in accordance with an embodiment of the invention. The process begins at initial step 87. The length ($L_{box}$) of the bounding box that was generated in step 41 (FIG. 2) is recorded.

Next, at step 89. A catheter is selected from a list of available catheters. The length of the selected catheter is known.

Next, at step 91 the difference between the length of the catheter and the length of the bounding box ($L_{box}-L_{cath}$) is stored.

Only those catheters having lengths that fall within a predetermined range from the length of the bounding box are given further consideration. At decision step 93, it is determined if the difference obtained in step 91 is greater than a lower limit and less than an upper limit of the range. A suitable range in mm is:

$$-3<(S_{box}-S_{cath})<+6.$$

If the determination at decision step 93 is affirmative, then control proceeds to step 95. The current catheter is added to a list of qualified catheters.

After performing step 95 or if the determination at decision step 93 is negative, control proceeds to decision step 97, where it is determined if more catheters are available for evaluation. If the determination at decision step 97 is affirmative, then control returns to step 89 to select another catheter.

If the determination at step 95 is negative, then at decision step 99, it is determined if the set of qualified catheters is empty, i.e., no qualified catheters were found. If the determination is affirmative, then control proceeds to final step 101 where failure is reported. No catheters matching the particular left atrium were found. However, the user may be able to manually select a suboptimum model in some cases.

If the determination at decision step 99 is affirmative, then control proceeds to step 103. The two short dimensions (width (y) and height (z)) of the bounding box are obtained ($S_{box(y)}$ and $S_{box(z)}$).

Next, at step 105 A catheter is selected from the list of qualified catheters that was compiled in step 95. Then at step 109 its two minor semi-axes are obtained ($S_{cath(y)}$; $S_{cath(z)}$). Each axis of the bounding box is evaluated with respect to the corresponding axis of the catheter.

Next at decision step 111 it is determined if the values $S_{cath(y)}-S_{box(y)}$ and $S_{cath(z)}-S_{box(z)}$ are both within an acceptable range in mm. The range can be from −3 mm to +3 mm.

If the determination at decision step 111 is negative, then control proceeds to step 113. The current catheter is removed from the list of qualified catheters and eliminated from further consideration.

If the determination at decision step 111 is affirmative, then at step 114 a value $S=(S_{box(y)}-S_{cath(y)})+(S_{box(z)}-S_{cath(z)})+(L_{box}-L_{cath})$ is computed for the current catheter.

After performing step 113 or step 114, then at decision step 115, it is determined if more members of the list of qualified catheters remain to be evaluated. If the determination is affirmative, then control returns to step 105.

If the determination at decision step 115 is negative, then control proceeds to final step 117. The catheter most closely approximating the left atrium, i.e., the catheter for which the value S computed in step 114 is closest to zero is reported to the operator. Several next-best matches may optionally be reported.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method for catheter contact optimization, the method comprising the steps of:
constructing a left atrial model of a heart of a living subject, the heart having a left atrium, an interatrial septum and a foramen ovale in the septum, including forming a three-dimensional bounding box with a center corresponding to a center of mass of the left atrium, the bounding box having a length, width and height;
selecting a global catheter from a database of global catheters that is dimensioned to conform to the left atrial model, the catheter having a length axis, the global catheter having a size that fits within a first predetermined range of the bounding box;
representing the catheter in the left atrial model by mapping the selected catheter to an ellipsoid and determining if the ellipsoid fits within a second predetermined range of the bounding box;
in the left atrial model extending the length axis of the catheter to form an intersection with the foramen ovale; and
reporting the intersection as a recommended site of transseptal puncture for insertion of the catheter therethrough.

* * * * *